United States Patent [19]
Wagner et al.

[11] Patent Number: 6,139,586
[45] Date of Patent: Oct. 31, 2000

[54] PROSTHESIS BRAKE JOINT

[75] Inventors: Helmut Wagner; Manfred Krukenberg, both of Duderstadt, Germany

[73] Assignee: Otto Bock Orthopaedische Industrie Besitz- und Verwaltungs-Kommanditgesellschaft, Duderstadt, Germany

[21] Appl. No.: 09/266,008

[22] Filed: Mar. 11, 1999

[30] Foreign Application Priority Data

Mar. 11, 1998 [DE] Germany .......................... 198 10 385

[51] Int. Cl.⁷ ..................................................... A61F 2/64
[52] U.S. Cl. ............................................... 623/44; 623/43
[58] Field of Search ................................... 623/43, 44, 45, 623/40; 403/91

[56] References Cited

U.S. PATENT DOCUMENTS

| | | | |
|---|---|---|---|
| 4,451,939 | 6/1984 | Thompson | 623/44 |
| 5,755,813 | 5/1998 | Krukenbera | 623/44 |

FOREIGN PATENT DOCUMENTS

| | | |
|---|---|---|
| 76932 | 6/1919 | Germany . |
| 330285 | 12/1920 | Germany . |
| 331719 | 1/1921 | Germany . |
| 320013 | 4/1990 | Germany . |
| 191 11 890 | 3/1995 | Germany . |

Primary Examiner—Bruce Snow
Attorney, Agent, or Firm—Foley & Lardner

[57] ABSTRACT

The invention relates to a brake joint for a prosthesis, in particular, to a brake-action knee joint for a leg prosthesis. There is an upper joint part, a lower joint part, and a joint shaft for pivotally connecting the upper and lower joint parts. The joint shaft is connected to the lower joint part in a rotatably fixed manner and is designed as a brake shaft. The joint shaft is surrounded by a brake arrangement, which bears upon the joint shaft it and is arranged in a cylindrical recess, which, together with the joint shaft, forms an annular chamber in a clamping part forming a central joint part. The upper joint part is mounted to the clamping part in an articulated manner via a pivot pin in such a way that the upper joint part, when loaded, impacts on the clamping part and thus the brake arrangement and thereby exerts a braking action on the joint shaft. To improve the brake arrangement, the invention proposes that the brake arrangement be formed by needle rollers, which are arranged with their axes parallel to the joint shaft. The needle rollers surround the joint shaft about its entire circumference and comprise an inner needle-roller ring, which bears on the joint shaft, and an outer needle-roller ring, which bears on the outer circumferential surface of the annular chamber and whose needle rollers engage like teeth between the inner needle rollers, and by an indexing wedge which sits on the upper joint part. When the upper joint part is loaded, in an approximately radial direction of action relative to the joint shaft, the indexing wedge presses apart two adjacent inner needle rollers in the circumferential direction of the joint shaft.

21 Claims, 8 Drawing Sheets

PROSTHESIS BRAKE JOINT

SUMMARY OF THE INVENTION

1. Field of the Invention

The invention relates to a prosthesis brake joint, in particular, to a brake-action knee joint for a leg prosthesis.

2. Description of Related Art

A prosthetic knee joint, like the one disclosed in DE 195 11 890 C1, has an upper joint part, a lower joint part, and a joint shaft which pivotally connects the upper and lower joint parts to one another. The joint shaft is connected to the lower joint part in a rotatably fixed manner. The joint shaft is designed as a brake shaft and is surrounded by a brake arrangement which bears upon the joint shaft. The brake arrangement is arranged in a cylindrical recess which, together with the joint shaft, forms an annular chamber in a clamping part. There is a central joint part, on which the upper joint part is mounted in an articulated manner via a pivot pin in such a way that the upper joint part, when loaded, impacts on the clamping part and thus the brake arrangement and thereby exerts a braking action on the joint shaft. Here, from the point of view of kinematics, the upper joint part and lower joint part can be changed around, with the joint shaft then being connected to the upper joint part in a rotatably fixed manner.

The brake arrangement has a brake bushing that runs upon the joint shaft in a bearing-like manner and is connected in a rotatably fixed manner to the clamping part. The brake bushing is surrounded by a circular brake chamber, which is filled with an incompressible medium, in fluid communication with a closed hollow space integrated in the clamping part. A pressure piston protrudes into the brake bushing thereby impacting the incompressible medium. The upper joint part is supported by the clamping part.

The difficulties suggested in the preceding are not intended to be exhaustive but rather are among many which tend to reduce the effectiveness in prosthetic brake joints. Other noteworthy problems may also exist; however, those presented above should be sufficient to demonstrate that such methods and apparatuses appearing in the past will admit to worthwhile improvement.

SUMMARY OF THE INVENTION

Accordingly, it is a general object of the invention to provide a brake joint for a prosthesis that will obviate or minimize the difficulties of the type previously described.

It is a specific object of the invention to provide a brake joint for a prosthesis that responds quickly.

It is another object of the invention to provide a brake joint for a prosthesis that exerts a high braking force.

It is still another object of the invention to provide a brake joint for a prosthesis that does not wear quickly.

A preferred embodiment of the invention intended to accomplish at least some of the foregoing objects includes an upper joint part and a lower joint part; a joint shaft pivotally connecting the upper and lower joint parts; and a plurality of inner needle rollers and a plurality of outer needle rollers surrounding the joint shaft; wherein each outer needle roller engages in between two of the plurality of inner needle rollers and an axis of each needle roller is parallel to an axis of the joint shaft.

Additional objects of the invention will be set forth in the following description, and, in part, will be obvious from the description, or may be learned by practice of the invention.

The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and, together with the general description given above and the detailed description of the preferred embodiments given below, serve to explain the principles of the invention.

DETAILED DESCRIPTION OF THE PREFERRED EMBODIMENTS

The objects are achieved by providing a brake arrangement having needle rollers, which are arranged with their axes parallel to the joint shaft, that surround the joint shaft about its entire circumference and comprise an inner needle-roller ring, which bears on the joint shaft, and an outer needle-roller ring, which bears on the outer circumferential surface of the annular chamber and whose needle rollers engage like teeth between the inner needle rollers, and by an indexing wedge, which sits on the upper joint part and which, when the upper joint part is loaded, in an approximately radial direction of action, relative to the joint shaft, presses apart two adjacent inner needle rollers in the circumferential direction of the joint shaft.

In the first preferred embodiment, as detailed above, it is preferable if the inner needle rollers, which are arranged at a clear circumferential distance from each other, have the same diameter. Here, the diameter of the outer needle rollers can correspond to that of the inner needle rollers. The indexing wedge preferably bears with a form-fit on an outer needle roller.

To ensure that the needle rollers of the inner needle-roller ring do not touch (which could happen with an axial offset), it is expedient that the inner and the outer needle rollers are guided radially with play between ball-bearing races.

In a modified embodiment, it is advantageous if the inner needle-roller ring has needle rollers of alternately smaller and greater diameter. The needle rollers of greater diameter function as spacers between the needle rollers of smaller diameter and lie on the outer circumferential surface of the annular chamber. The outer needle ring has needle rollers only of smaller diameter, each of which engages a needle roller of greater diameter and, in the bending direction, a needle roller of smaller diameter of the inner needle roller ring.

To ensure a quick response of the brake arrangement, it is advantageous if the radial height of the annular chamber is only a few tenths of a millimeter smaller than the sum of the diameters of the two superposed needle rollers of smaller diameter.

Referring now to the Figures, wherein like numerals represent like parts, there will be seen an upper joint part 1, a lower joint part 2 and a joint shaft 3. The joint shaft 3 pivotally connects the upper and lower joint parts 1, 2 to one another. The joint shaft, which is connected to the lower joint part 2 in a rotatably fixed manner, is designed as a brake shaft and is mounted between the outer shaft bearings 4. A clamping part 5, which forms a central joint part, surrounds the joint shaft 3 concentrically with a cylindrical recess and forms, with the joint shaft, an annular chamber 6. The brake arrangement is arranged in the annular chamber 6. The upper joint part 1 is mounted in an articulated manner on the clamping part 5 via a pivot pin 7.

In the first preferred embodiment, as show in FIGS. 1 through 5, the brake arrangement is formed by needle rollers 8, 9, which are arranged with their axes parallel to the joint shaft 3. The needle rollers 8, 9 surround the joint shaft about its entire circumference and define an inner needle-roller ring, which bears on the joint shaft 3, and an outer needle-roller ring, which bears on the outer circumferential surface of the annular chamber 6. The outer needle rollers 9 engage like teeth between the inner needle rollers 8. The inner needle rollers 8 each have the same diameter and are arranged at clear circumferential distance from one another. The diameter of the outer needle rollers 9 corresponds to that of the inner needle rollers 8. The inner needle rollers 8 are, like the outer needle rollers 9, guided radially with play between ball-bearing races (not show in detail).

A downwardly projecting indexing wedge 10 sits on the upper joint part 1 and bears with a form-fit on an outer needle roller 9. When the upper joint part 1 is loaded, in an approximately radial direction of action relative to the joint shaft 3, indexing wedge 10 presses two adjacent inner needle rollers 8 apart in the circumferential direction of the joint shaft 3. The resultant wedging effect between the inner and outer needle rollers 8, 9 causes a clamped connection between the upper joint part 1 and the joint shaft 3 and thus to a blocking of flexion.

Figure 1:
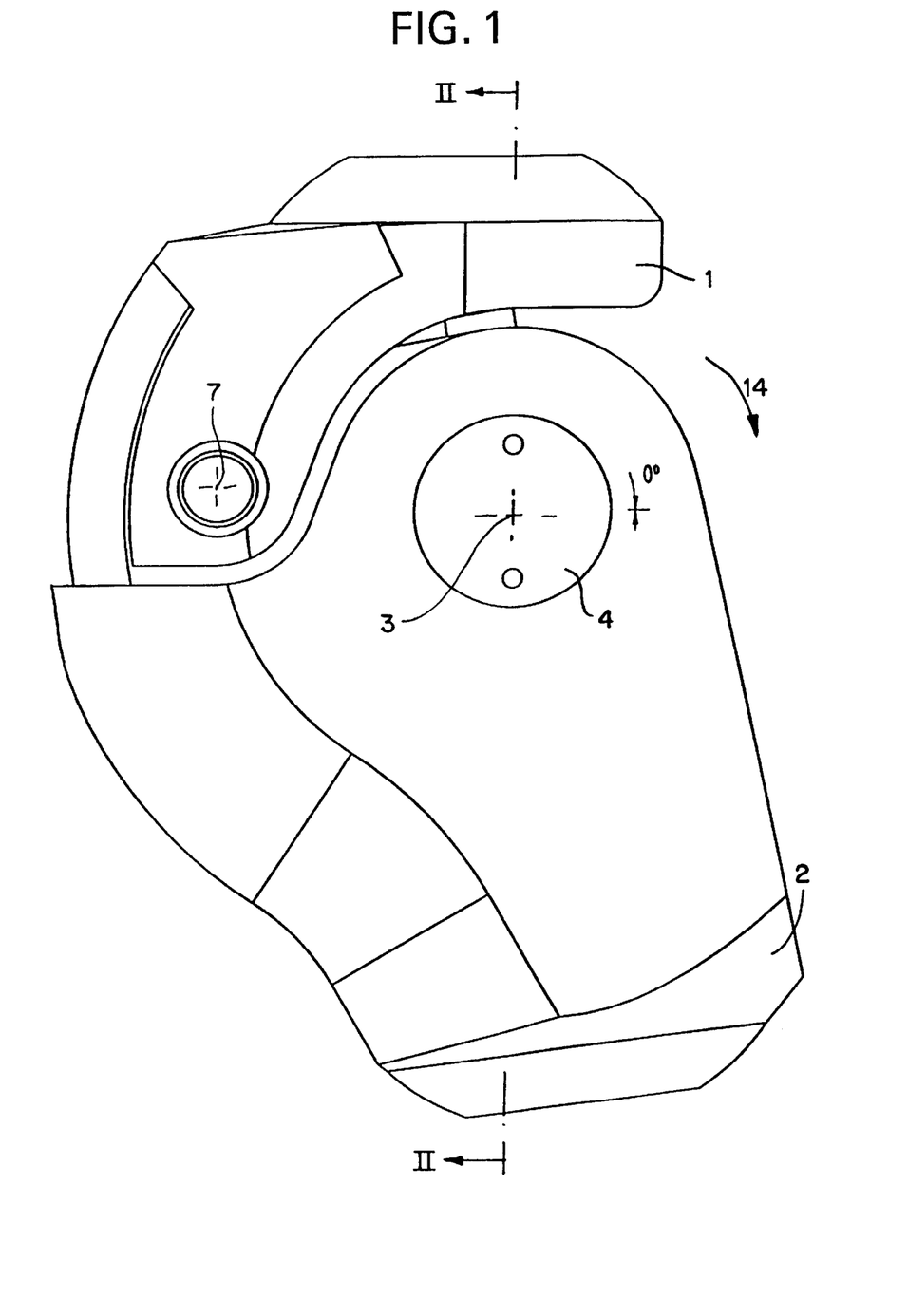
FIG. 1 is a side view of a brake-action knee joint in the extended position.
Figure 2:
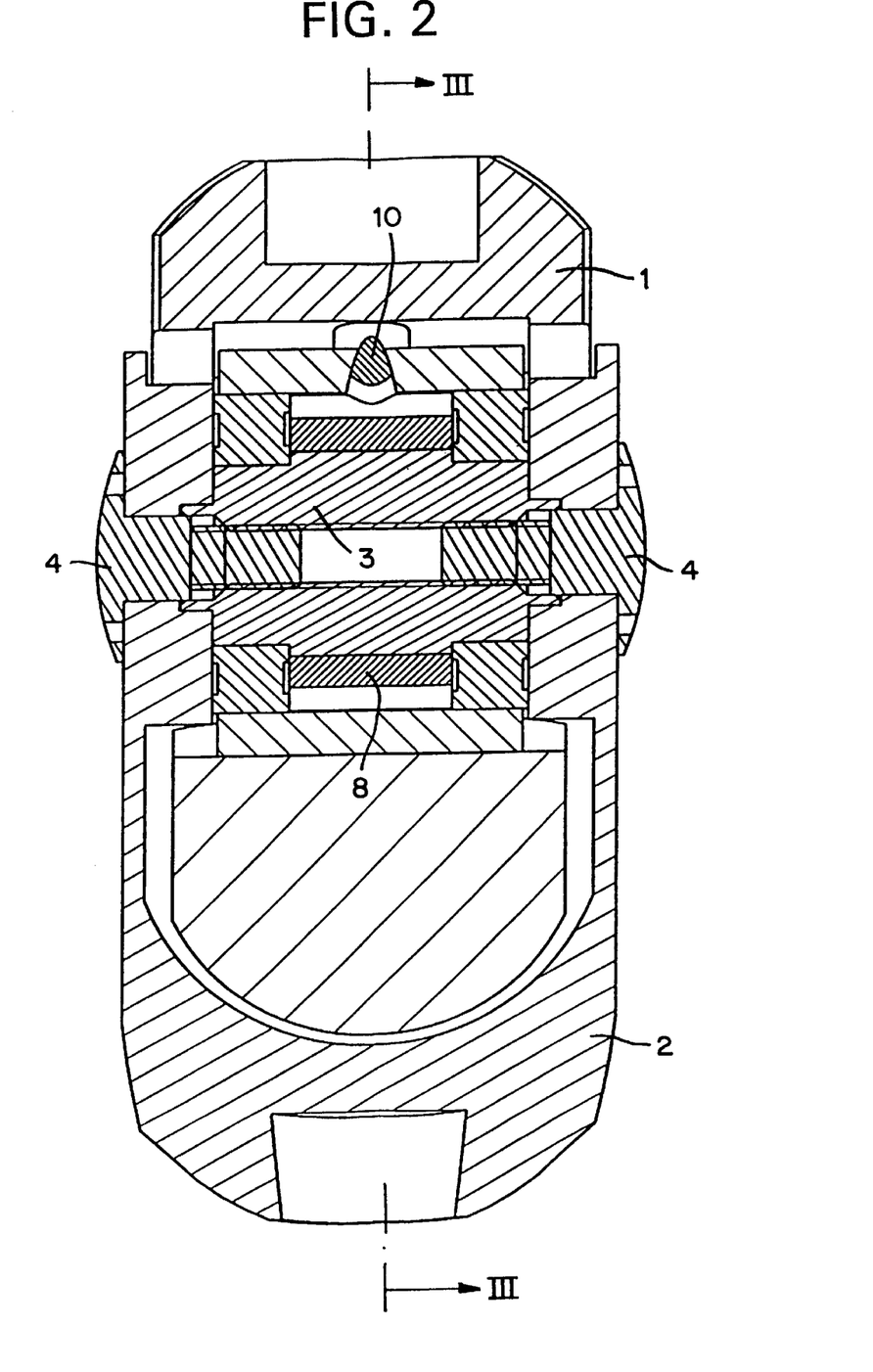
FIG. 2 is a vertical section along the line II—II in FIG. 1.
Figure 3:
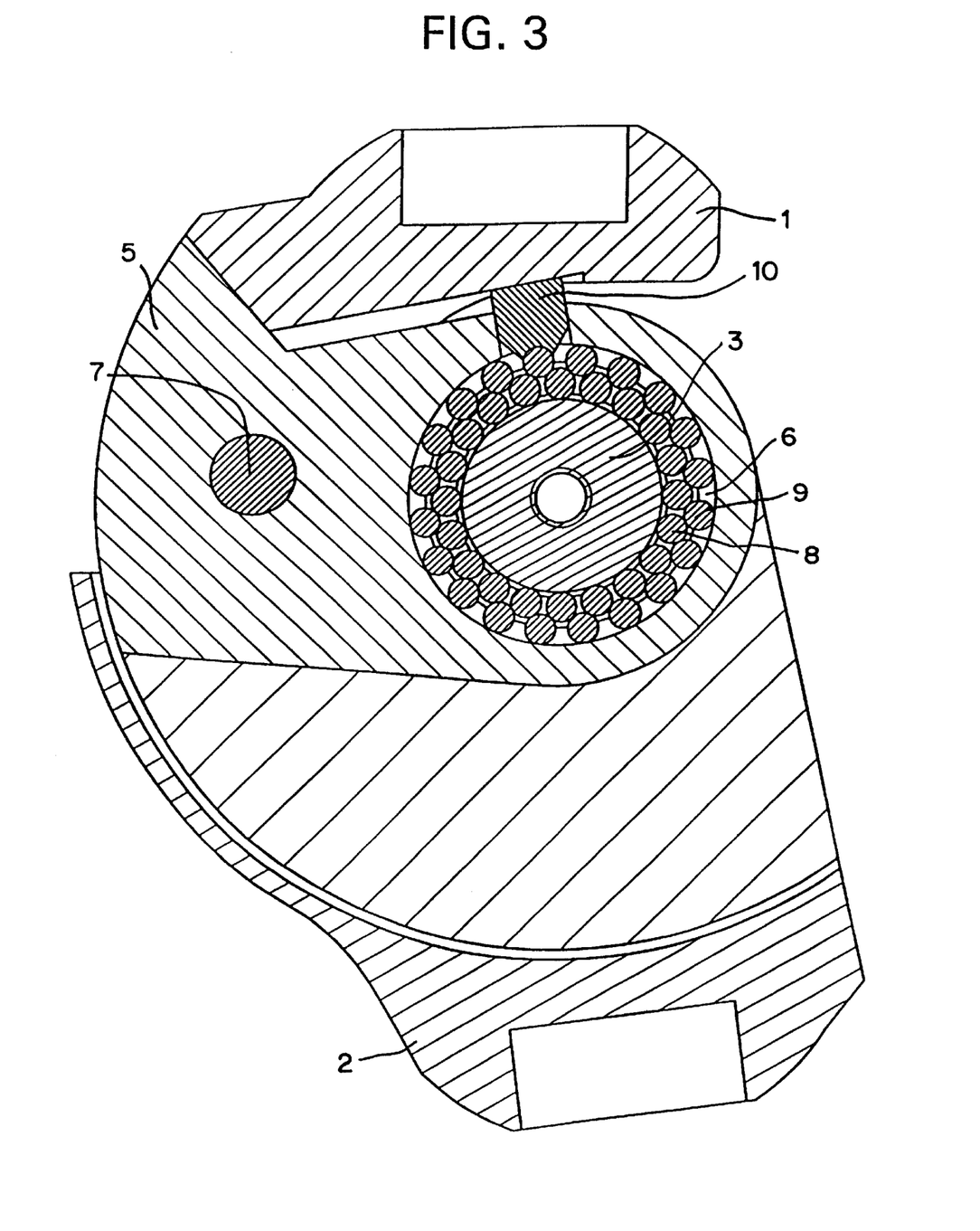
FIG. 3 is a vertical section along the line III—III in FIG. 2.
Figure 4:
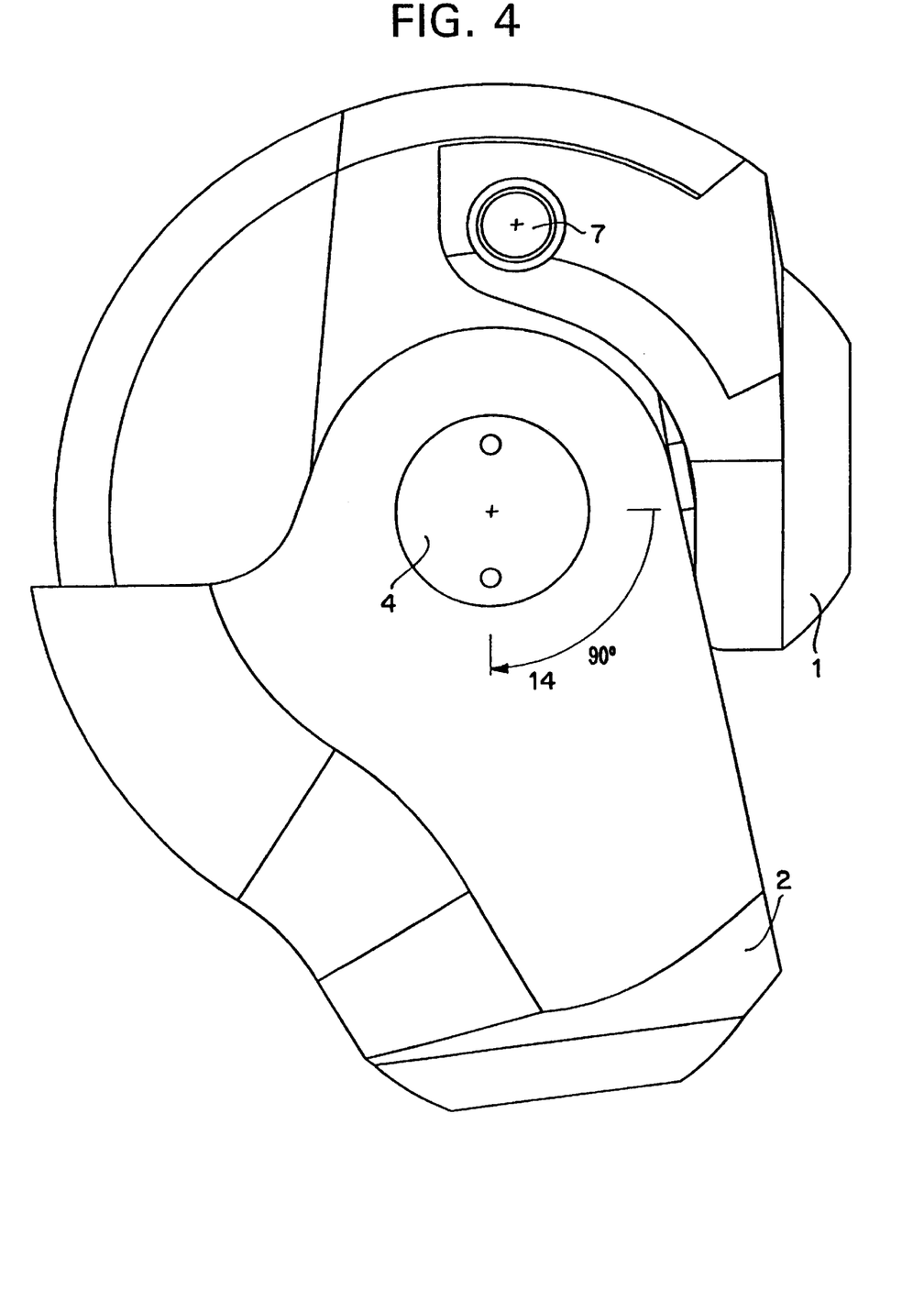
FIG. 4 is the brake-action knee joint according to FIG. 1 in the flexed position.
Figure 5:
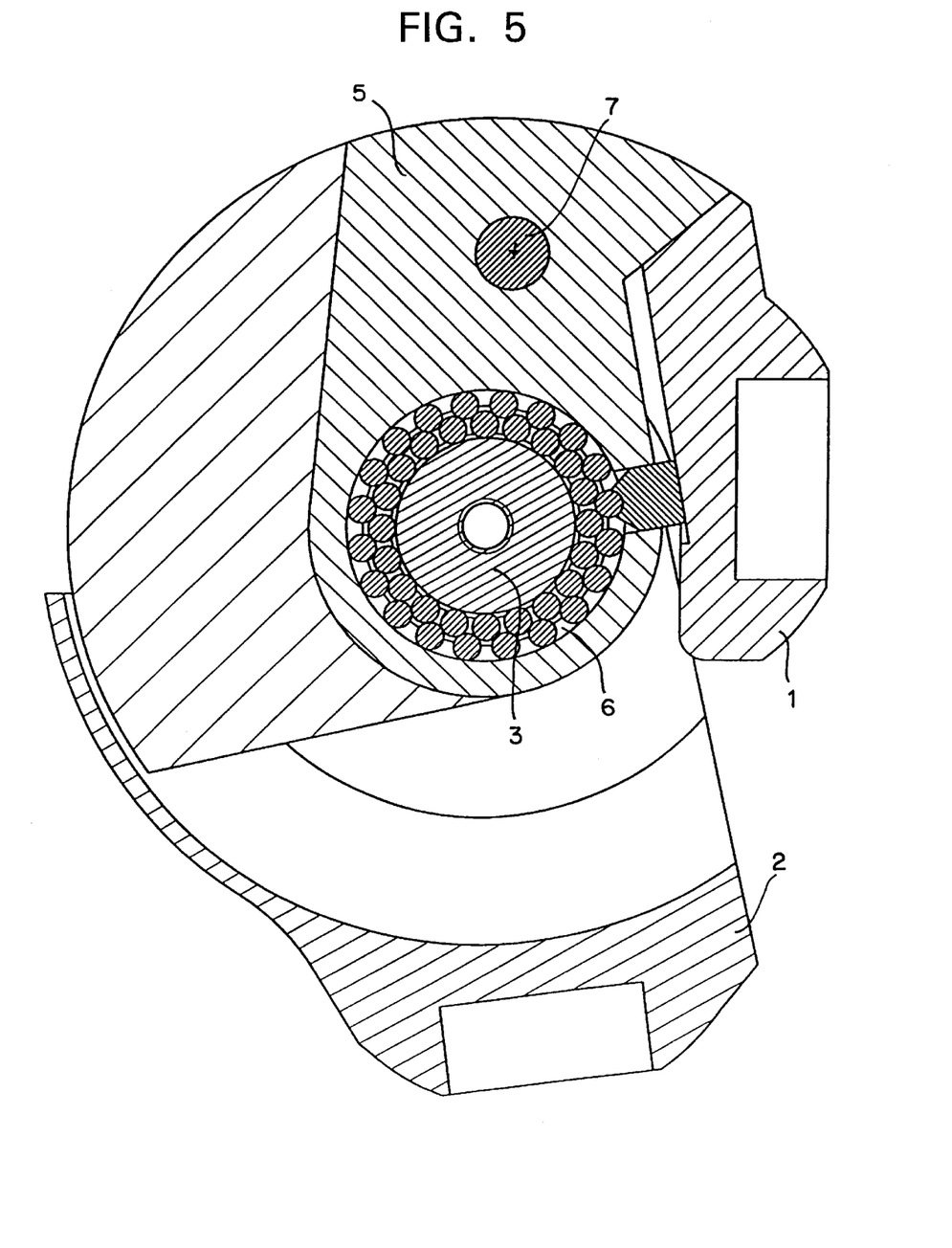
FIG. 5 is a section according to FIG. 3 through the flexed brake-action knee joint according to FIG. 4.
Figure 6:
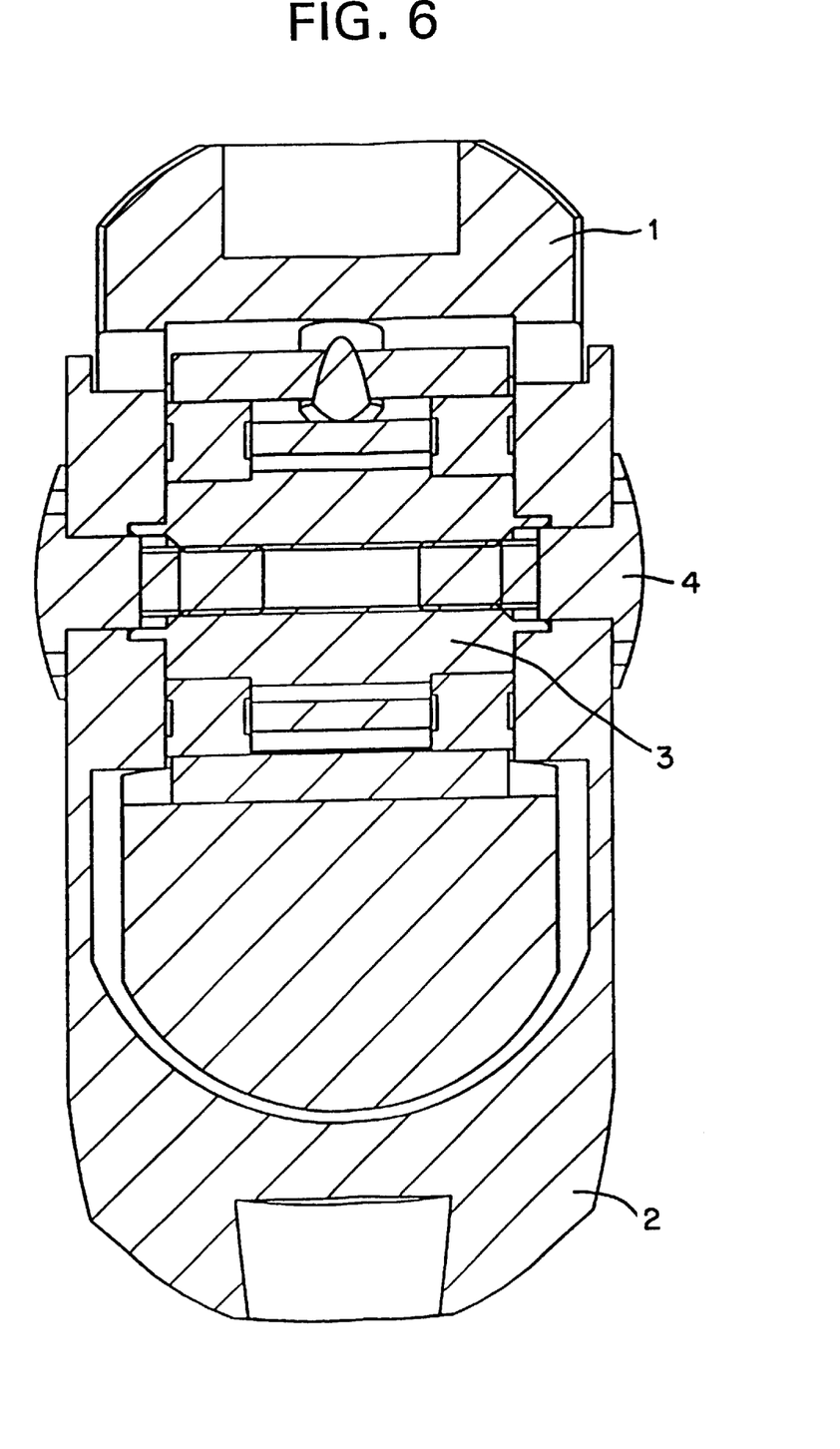
FIG. 6 is, in a representation according to FIG. 2, a section through a modified embodiment.
Figure 7:
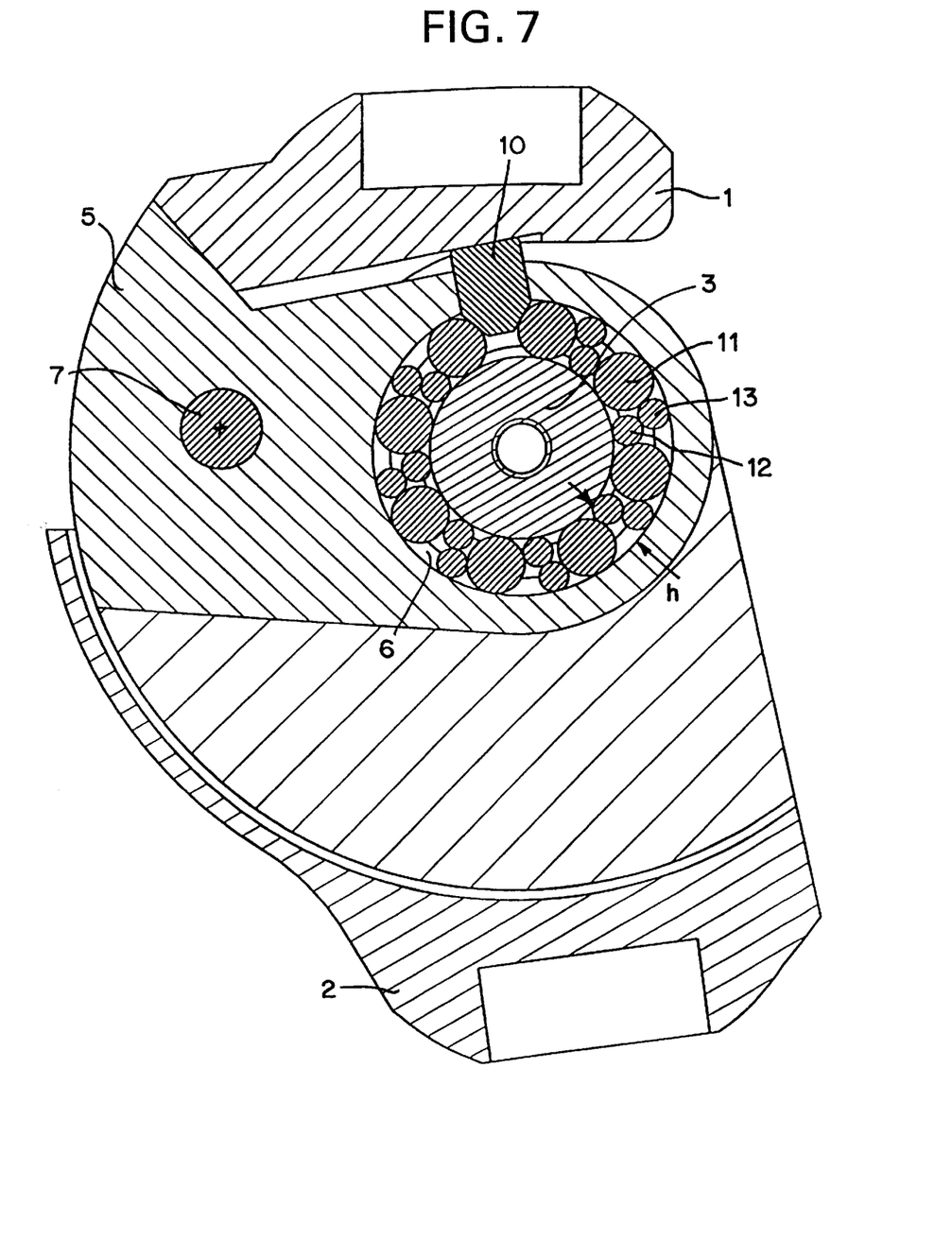
FIG. 7 is the brake-action knee joint according to FIG. 6 in a section according to FIG. 3.
Figure 8:
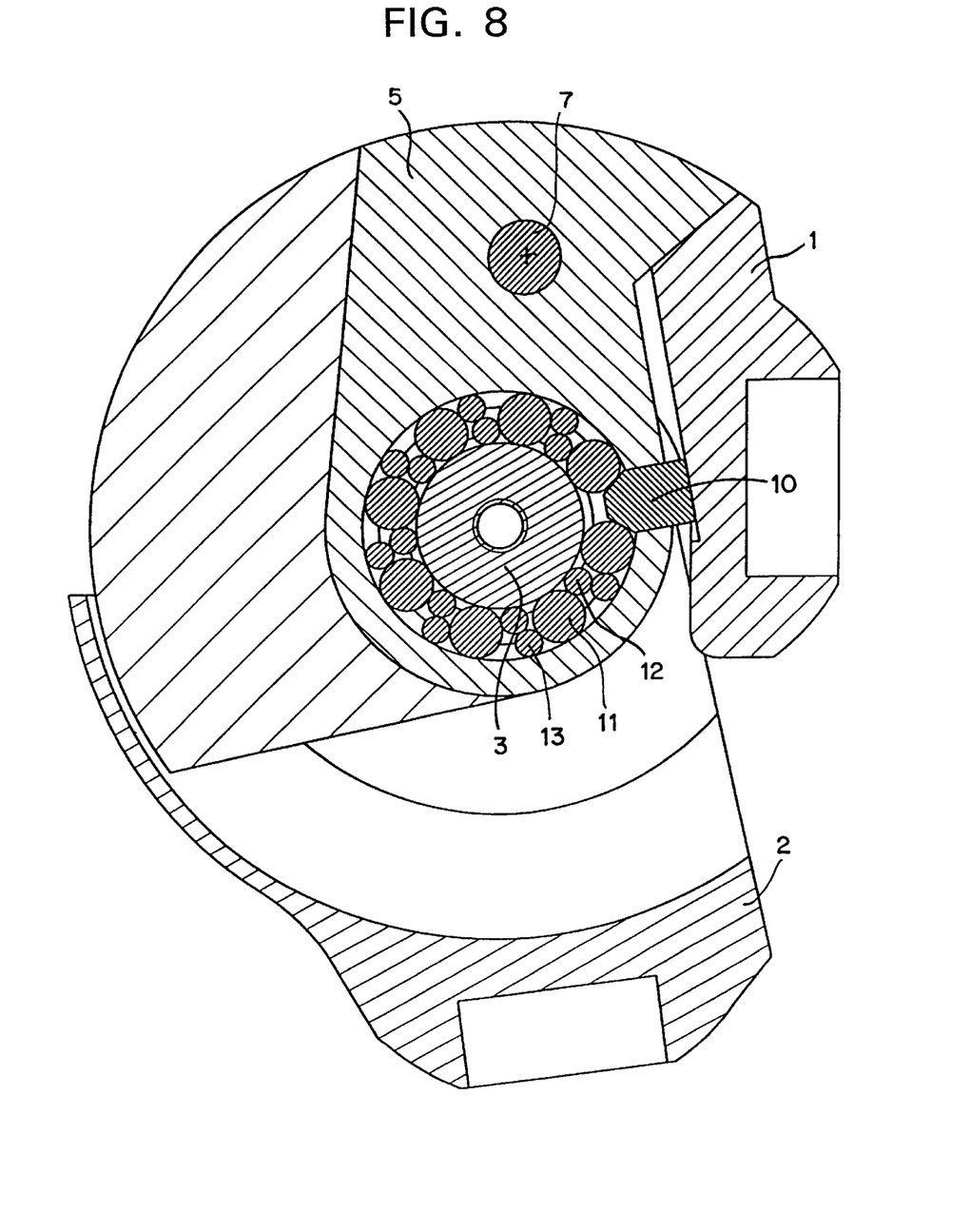
FIG. 8 is the brake-action knee joint according to FIG. 7 in the flexed position.

In the second preferred embodiment according to FIGS. 6 through 8, the inner needle roller ring is made up of needle rollers of alternately smaller and greater diameter. The needle rollers 11 of greater diameter function as spacers between the needle rollers 12 of smaller diameter and lie on the outer circumferential surface of the annular chamber 6. The outer needle ring is defined by needle rollers 13 of only smaller diameter. Each outer needle roller 13 engages between an inner needle roller 11 of greater diameter and, following the latter in the direction of flexion 14, an inner needle roller 12 of smaller diameter. In the illustrative embodiments shown, the needle rollers 12 and 13 of smaller diameter each have the same diameter.

The radial height h of the annular chamber 6 is only a few tenths of a millimeter smaller than the sum of the diameters of the two superposed needle rollers 12, 13 of smaller diameter. If, for example, the diameter of the needle rollers 12, 13 is 3 mm, then the gap height h of the annular chamber 6 is preferably 5.8 mm. FIG. 7 shows that the roller pairs 12, 13 have an angle of incidence counter to the bending direction 14.

In the second illustrative embodiment the indexing wedge 10 has a beveled surface. The indexing wedge 10 acts on two adjacent needle rollers 11 of greater diameter and thereby impacts them—counter to each other—in the circumferential direction of the annular chamber 6.

In both illustrative embodiments, the circumferential surface of the joint shaft 3 and/or of the annular chamber 6 can be hardened.

In both embodiments, the needle rollers lead to an exact adjustment of the joint shaft 3. In the first illustrative embodiment, a slightly higher pressure is needed via the indexing wedge 10 to elicit the response of the brake arrangement. The brake arrangement in the second illustrative embodiment responds even at slight pressures. In the first illustrative embodiment, a loading of the upper joint part 1 leads to blocking of the upper joint part 1 relative to the joint shaft 3, in both the bending and extending directions. On the other hand, in the second preferred embodiment, the blocking is effective only in the bending direction 14.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

Priority document, DE 198 10 385.9, filed Mar. 11, 1998, is hereby incorporated by reference.

What is claimed is:

1. A brake joint for a prosthesis, comprising:
   an upper joint part and a lower joint part;
   an indexing wedge mounted to the upper joint part;
   a joint shaft pivotally connecting the upper and lower joint parts; and
   a plurality of inner needle rollers and a plurality of outer needle rollers surrounding the joint shaft;
   wherein each outer needle roller is engaged between two of the plurality of inner needle rollers; and
   wherein an axis of each needle roller is parallel to an axis of the joint shaft.

2. A brake joint for a prosthesis as claimed in claim 1, wherein a diameter of the inner needle rollers is constant.

3. A brake joint for a prosthesis as claimed in claim 2, wherein a diameter of the inner needle rollers is equal to a diameter of the outer needle rollers.

4. A brake joint for a prosthesis as claimed in claim 3, wherein a circumferential distance between each of the inner needle rollers is constant.

5. A brake joint for a prosthesis as claimed in claim 3, wherein a surface of the indexing wedge corresponds to an outer surface of the outer needle rollers.

6. A brake joint for a prosthesis as claimed in claim 3, wherein the indexing wedge acts on one of the plurality of outer needle rollers when the upper joint part is in a loaded condition.

7. A brake joint for a prosthesis as claimed in claim 6, wherein the outer needle roller that is being acted on presses two adjacent inner needle rollers apart and causes a clamping effect between the upper joint part and the joint shaft.

8. A brake joint for a prosthesis as claimed in claim 1, wherein the plurality of inner needle rollers have a small and a large diameter.

9. A brake joint for a prosthesis as claimed in claim 8, wherein the plurality of inner needle rollers are arranged such that the small and large diameters alternate.

10. A brake joint for a prosthesis as claimed in claim 8, wherein the large diameter inner needle rollers act as spacers.

11. A brake joint for a prosthesis as claimed in claim 10, wherein each outer needle roller engages between an inner needle roller of large diameter and an inner needle roller of small diameter.

12. A brake joint for a prosthesis as claimed in claim 9, wherein a diameter of the outer needle rollers equals the diameter of the small inner needle roller.

13. A brake joint for a prosthesis as claimed in claim 8, wherein the indexing wedge has a beveled surface.

14. A brake joint for a prosthesis as claimed in claim 13, wherein the indexing wedge acts on two adjacent large diameter inner rollers.

15. A brake joint for a prosthesis as claimed in claim 1, wherein a surface of the joint shaft is hardened.

16. A brake joint for a prosthesis, comprising:

an upper joint part;

a lower joint part pivotally connected to the upper joint part by a joint shaft;

a clamping part surrounding the joint shaft and forming an annular chamber;

an inner needle-roller ring acting on the joint shaft and having a plurality of inner needle rollers of equal diameter;

an outer needle-roller ring acting on an inner surface of the annular chamber and having a plurality of outer needle rollers; and an indexing wedge contacting the upper joint part and projecting downward;

wherein a diameter of the outer needle rollers is equal to the diameter of the inner needle rollers; and wherein each outer needle roller engages between adjacent inner needle rollers.

17. A brake joint for a prosthesis as claimed in claim 16, wherein a distance between each of the inner needle rollers in a circumferential direction is equal.

18. A brake joint for a prosthesis as claimed in claim 16, wherein the indexing wedge is formed to fit to the upper needle rollers and presses two adjacent inner needle rollers apart in the circumferential direction when the upper joint part is in a loaded condition.

19. A brake joint for a prosthesis, comprising:

an upper joint part;

a lower joint part pivotally connected to the upper joint part by a joint shaft;

a clamping part surrounding the joint shaft and forming an annular chamber;

an inner needle-roller ring acting on the joint shaft and having a plurality of inner needle rollers of alternate small and large diameters;

an outer needle-roller ring acting on an inner surface of the annular chamber and having a plurality of outer needle rollers; and an indexing wedge contacting the upper joint part and projecting downward;

wherein a diameter of the outer needle rollers is equal to the diameter of the small diameter inner needle rollers;

wherein the large diameter inner needle rollers act on the inner surface of the annular chamber; and wherein each outer needle roller engages between a large diameter needle roller and a small diameter needle roller.

20. A brake joint for a prosthesis as claimed in claim 19, wherein a radial height of the annular chamber is smaller than a sum of the diameter of each outer needle roller and the diameter of each small diameter inner needle roller.

21. A brake joint for a prosthesis as claimed in claim 20, wherein a surface of the indexing wedge is beveled and acts on two adjacent large diameter inner needle rollers.

* * * * *